United States Patent
Oliver et al.

(10) Patent No.: US 8,354,773 B2
(45) Date of Patent: Jan. 15, 2013

(54) COMPOSITE ACOUSTIC ABSORBER FOR ULTRASOUND TRANSDUCER BACKING MATERIAL

(75) Inventors: Nelson H. Oliver, Sunnyvale, CA (US); Diana M. Tasker, Fair Oaks, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2223 days.

(21) Appl. No.: 10/646,222

(22) Filed: Aug. 22, 2003

(65) Prior Publication Data
US 2005/0043625 A1 Feb. 24, 2005

(51) Int. Cl.
*H01L 41/00* (2006.01)
(52) U.S. Cl. .................................... 310/327
(58) Field of Classification Search ........ 310/320, 310/321, 327, 334; 600/459
See application file for complete search history.

(56) References Cited

U.S. PATENT DOCUMENTS

| | | | |
|---|---|---|---|
| 3,117,054 A * | 1/1964 | Antonucci ............ | 428/317.1 |
| 3,786,202 A * | 1/1974 | Schafft ............... | 310/324 |
| 3,794,866 A * | 2/1974 | McElroy et al. ........ | 310/327 |
| 4,373,401 A * | 2/1983 | Baumoel .............. | 73/861.18 |
| 4,382,201 A * | 5/1983 | Trzaskos ............. | 310/327 |
| 4,523,122 A * | 6/1985 | Tone et al. ........... | 310/334 |
| 4,528,652 A * | 7/1985 | Horner et al. ......... | 367/162 |
| 4,571,520 A * | 2/1986 | Saito et al. .......... | 310/327 |
| 4,779,244 A | 10/1988 | Horner et al. | |
| 4,800,316 A | 1/1989 | Ju-Zhen | |
| 5,297,553 A | 3/1994 | Sliwa, Jr. et al. | |
| 5,378,733 A | 1/1995 | Bates et al. | |
| 5,655,538 A | 8/1997 | Lorraine et al. | |
| 5,664,456 A * | 9/1997 | Eckert ............... | 73/290 V |
| 5,852,860 A | 12/1998 | Lorraine et al. | |
| 6,002,196 A * | 12/1999 | Sumita et al. ........ | 310/326 |
| 6,278,224 B1 * | 8/2001 | Sawada et al. ........ | 310/334 |

* cited by examiner

*Primary Examiner* — Jacqueline Cheng

(57) ABSTRACT

A backing block composite is provided. A transducer is manufactured to include the backing block of composite material. One constituent material provides a skeleton or matrix for enclosing volumes or pockets of another material. The materials are incompatible for bonding, so do not adhere to each other. For example, silicone microspheres are mixed with a nonsilicone resin, forming silicone pockets within the resin. Since the silicone does not adhere to the resin, the silicone may vibrate or otherwise move relative to the cured resin matrix, causing friction between the two materials. As acoustic energy propagates into the backing material, the composite structure of incompatible materials attenuates the acoustic energy as frictionally generated heat between the two material, or through other processes.

18 Claims, 3 Drawing Sheets

COMPOSITE ACOUSTIC ABSORBER FOR ULTRASOUND TRANSDUCER BACKING MATERIAL

BACKGROUND

The present invention relates to backing for transducers. In particular, an acoustic absorber is provided as a backing material.

Ultrasound transducers, such as used in medical diagnostic ultrasound imaging, include transducer elements for converting between electrical and acoustic energy. The transducer elements are manufactured to be positioned adjacent to a patient. Ultrasound energy travels from the transducer element through one or more matching layers into the patient. Responsive echos are then received by the transducers. When the transducer elements generate acoustic energy, the acoustic energy propagates from the element both towards and away from the patient due to expansion and contraction of the elements, generally along one dimension. The acoustic energy propagation towards the patient is desired; the acoustic energy propagating away from the patient is undesired. To absorb the undesired acoustic energy and prevent receiving echoes from clutter or structures outside of the patient, an acoustically absorptive backing block connects to the transducer.

Backing blocks include attenuative material for absorbing acoustic energy. Backing blocks are also frequently used as a rigid or semi-rigid support for the assembly of the ultrasound transducer stack of the transducer material and associated matching layers. For example, plasticized resins, such as epoxies, are used, because they can be both rigid and acoustically absorbing. Plasticizers are non-volatile solvents that increase the attenuation of the resin, based on intermolecular interaction. However, the plasticizer lowers the glass transition temperature, softening the resin on a microscopic level. Such resins are somewhat but generally not highly absorptive of ultrasound, and are somewhat but not particularly rigid. In practice, a balance is struck between rigidity and attenuation to make an acceptable transducer backer block. The balance may yield material that is marginally functional for both purposes. Rigid urethanes or polyesters have also been used for backing block materials.

Sound absorbers for walls have used different materials in combination to absorb sound. For example, lead spheres are coated with rubber and placed within an epoxy or foam. The lead is bonded to the rubber, and the rubber is bonded to the epoxy. Acoustic energy is then absorbed through relative motion of the ball bearings as compared with the epoxy matrix.

BRIEF SUMMARY

The present invention is defined by the following claims, and nothing in this section should be taken as a limitation on those claims. By way of introduction, the preferred embodiments described below include transducers for ultrasound transmission and reception, and methods of making transducers. The transducers include a backing block of composite material. One material provides a skeleton or matrix for enclosing volumes or pockets of another material. The materials display incompatible polarities, so do not adhere to each other. For example, silicone spheres are mixed with a polyester, polyurethane, or epoxy resin, forming silicone pockets within the resin. Since the silicone does not adhere to the resin, the silicone may vibrate or otherwise move relative to the resin, causing friction between the two materials. As acoustic energy propagates into the backing material, the composite structure of incompatible materials attenuates the acoustic energy through friction between the two materials, as well as other processes.

In a first aspect, an ultrasound transducer for ultrasound transmission or reception is provided. The ultrasound transducer includes at least one transducer element. A backing block is adjacent to the transducer element. The backing block is a composite of at least two materials. One of the materials includes a plurality of pockets of the other material.

In a second aspect, an ultrasound transducer for ultrasound transmission or reception is provided. A backing block is positioned adjacent to at least one transducer element. The backing block includes a composite of at least two materials. The materials are incompatible, unbound or free of mutual adhesion.

In a third aspect, an ultrasound transducer for ultrasound transmission or reception is provided. A backing block is positioned adjacent to at least one transducer element. The backing block is a composite of silicone and epoxy or other rigid-curing resin.

In a fourth aspect, a method for manufacturing an ultrasound transducer for ultrasound transmission and reception is provided. Pluralities of substantially solid particles of a first material are mixed with a liquid second material. The mixture is then cured. The cured mixture is connected as a backing block to a transducer. The materials are incompatible, unbound or free of mutual adhesion.

Further aspects and advantages of the invention are discussed below in conjunction with the preferred embodiments.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An ultrasound transducer includes one or an array of elements. Any of various arrangements of elements may be used, such as linear, curved linear, multi dimensional, various sparse or irregular element patterns, regular element patterns or other now known or later developed arrangement of elements. In one embodiment, the transducer is used for medical diagnostic ultrasound imaging, but transducers used for mechanical testing or other purposes may be provided. For medical imaging, the transducer is adapted for use external to or internal to the patient. For example, the transducer is used for hand held, catheter-mounted, trans-esophageal or endo-cavity uses.

Figure 1:
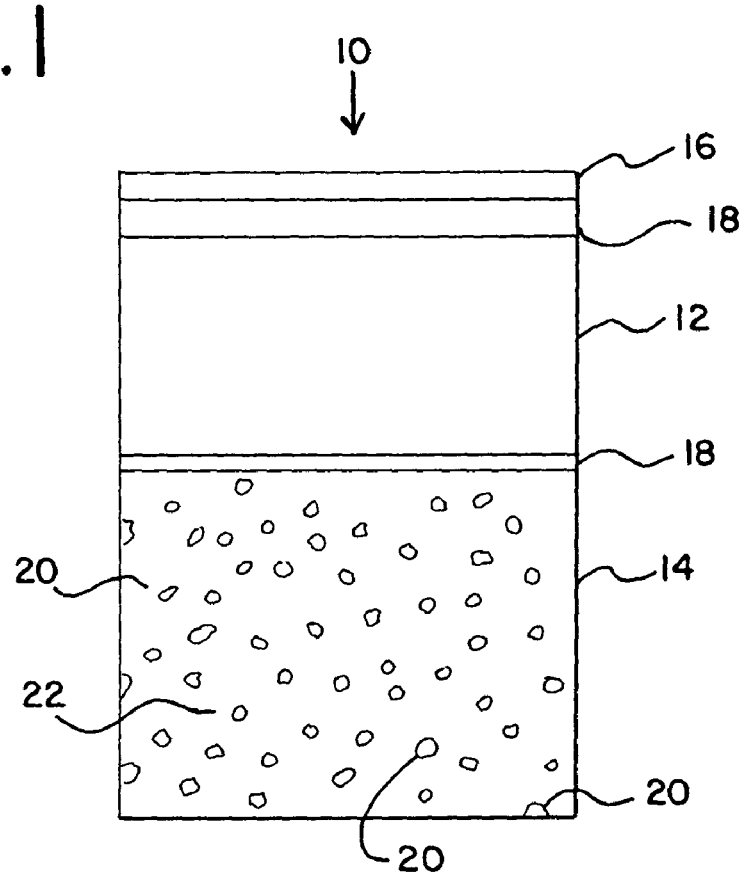
FIG. 1 is a cross-section view of one embodiment of an ultrasound element and associated backing block.

FIG. 1 shows a cross section of a transducer 10. The transducer 10 includes a stack of components. The components include a transducer element 12, a backing block 14, a matching layer 16 and a pair of electrodes 18 on different sides of the transducer element 12. Additional, different or fewer components may be provided, such as providing no or additional matching layers. As another example, a lens is provided above the matching layer 16. Different stack arrangements may be used, such as providing an electrode spaced away from the transducer element by one or more conductive matching layers 16.

The transducer element 12 is a piezoelectric (PZT) ceramic, PZT composite, microelectromechanical membrane, capacitive membrane ultrasound transducer, or other now known or later developed device for transducing between acoustic and electrical energies. The transducer element 12 is any of various shapes and sizes, such as being a cylinder, a rectangular post, having curved surfaces for frequency-dependent focusing, having stepped surfaces, having a varying thickness, or other now known or later developed element structures.

The electrodes 18 are provided on two different sides of the transducer 12 to generate electrical signals in response to acoustically-induced motion of the transducer element 12. The electrodes 18 also apply electrical energy to induce motion of the transducer element 12. The matching layer(s) 16 provide(s) an acoustic impedance matching network between the acoustic impedance of the element 12 and the patient.

The backing block 14 supports one or more elements 12. The elements 12 are directly or indirectly bonded to a top surface of the backing block 14. The backing block 14 is of a same width as the elements 12, but a greater or lesser width may be provided. The backing block 14 has a thickness that is the same, greater or lesser than the thickness of the element 12. The thickness is selected to provide sufficient structural support to an array of elements 12 on the backing block 14, and to sufficiently attenuate acoustic energy reflected from the backing block back surface, back toward the front surface while minimizing the size of the transducer. The thickness may vary as a function of any molding or casting structures for increasing rigidity, increasing attenuation, or other purposes. One or more stiffening inserts are optionally included within the backing block 14. In other embodiments, the backing block 14 includes two or more different structures having different attenuation and/or stiffness characteristics interwoven in a comb or honeycomb type pattern.

At least one material or structure of the backing block 14 is a composite material. The composite includes at least two different materials. One of the materials is incompatible with another of the materials. For example, both materials comprise different polymers that do not physically or chemically bond. In one embodiment, one material is a solid silicone and the other material is made from a liquid resin, such as a two-part epoxy. The silicone does not bond to the resin under normal circumstances. As a result, pluralities of pockets 20 of one (solid) material are enclosed within the other (castable) material. The pockets 20 are of any of various shapes, such as spheroids, whisker, elongated, cubic, polygon, platelet or irregular particle shapes. One embodiment comprises a small enough fraction of solidified resin in the composite that the composite structure is reduced to that of an open-celled or "reticulated" foam. One or more pockets may be on an edge or surface of the backing block 14 rather than enclosed within the other material. By constructing the backing block 14 out of incompatible or nonbonding materials, the enclosed material is permitted relative motion with respect to the surrounding material matrix. As a result, frictional heating is possible between the two materials in response to applied acoustic energy. Any frictional heating attenuates the acoustic energy. A disparity in hardness between the two nonbonded materials contributes to the relative motion when under an acoustic load. The difference in hardness may also contribute to the mechanism which attenuates the acoustic energy.

The composite of the backing block 14 is homogeneous on the scale of the internal acoustic wavelength. For typical medical ultrasound frequencies, the pockets are less than 20 microns along a longest or maximum dimension. In one embodiment, silicone rubber spheres of 13 microns or smaller are dispersed throughout a castable resin, such as a two-part epoxy. The size of the pockets of filler material is sized to be small enough to avoid undesirable scattering at higher ultrasound frequencies likely to be used, and dispersed to provide a homogeneous or substantially homogeneous composite on the scale of the wavelength of the likely frequencies to be used.

The matrix material 22 of the composite interconnects throughout the backing block 14. As a result, the backing block 14 has a stiffness or rigidity characteristic of the skeleton or matrix of interconnected material, i.e. the cured-resin phase. In one embodiment, the resin or all materials of the composite are substantially free of plasticizer. For example, the resin includes a two-part epoxy composed of a resin and a hardener without plasticizers. As a result, the rigidity of the resin is higher than as would be with included plasticizer. In alternative embodiments, a plasticizer is included within one or both materials of the composite. In conventional backing blocks 14, the plasticized resin allows friction between polymer molecules for attenuating acoustic energy. Without the plasticizer, attenuation is provided by the friction generated between the filler material in the pockets 20 and the cured resin material of the matrix 22.

The materials of the composite have substantially different hardnesses but substantially the same acoustic impedance in one embodiment. For example, silicone is soft as compared to typical cured epoxy resin, but has substantially the same acoustic impedance at ultrasound frequencies, such as about 1-2½ MRayl. Since comparable impedances are provided, undesirable scattering is reduced. Different materials with different relative acoustic impedances may be provided. For example the acoustic impedance of one material is within forty percent, ten percent or other percentage of the acoustic impedance of the other material. The acoustic impedance of the composite material of the backing block 14 using silicone filler particles and an epoxy resin is about 1.5 MRayl. Different acoustic impedances may be provided by including fillers or other materials. The similarity in acoustic impedances is provided by using materials of a similar density and velocity. For example, the density of one material of the composite is within ten percent of the density of another material. Using the example embodiment of silicone particles in resin, both materials of the composite have about a 1.1 or 1.2 gram/cc density. In one embodiment, each of the materials is provided in a substantially equal fractional volume. For example, the volume of one material is within ten percent of the volume of another material. Different ratios of density, volume and acoustic impedance may be provided. Differences in volume and density or mass inter-relate between the purposes of providing rigidity and acoustic attenuation while avoiding scattering. Various combinations of different materials of different densities or volumes may be used, such as with differences greater than ten percent. The volumes and distribution are experimentally determined. The regularity of the shape of the pockets 20 may also affect one or more of the performance characteristics associated with the purposes of the backing block 14.

In the silicone and epoxy composite backing block 14 example discussed above, high attenuation with low creep is provided. At 37° C., the attenuation at 2 megahertz may be about 15 dB/mm. Longitudinal acoustic impedance is about 1.7 MRayl. At about 5 megahertz, the acoustic attenuation is about 40 dB/mm, i.e., 1 dB/mil. Where no plasticizer is used, the resin matrix or skeleton 22 is less likely to elastically deform at modest temperatures and pressures. Unlike typical backing materials that have a glass transition temperatures below 70° C. due to the plasticizer, the glass transition temperature of the resin free of plasticizer is higher, avoiding creep or deformation during elevated-temperature processing such as bonding.

Figure 3:
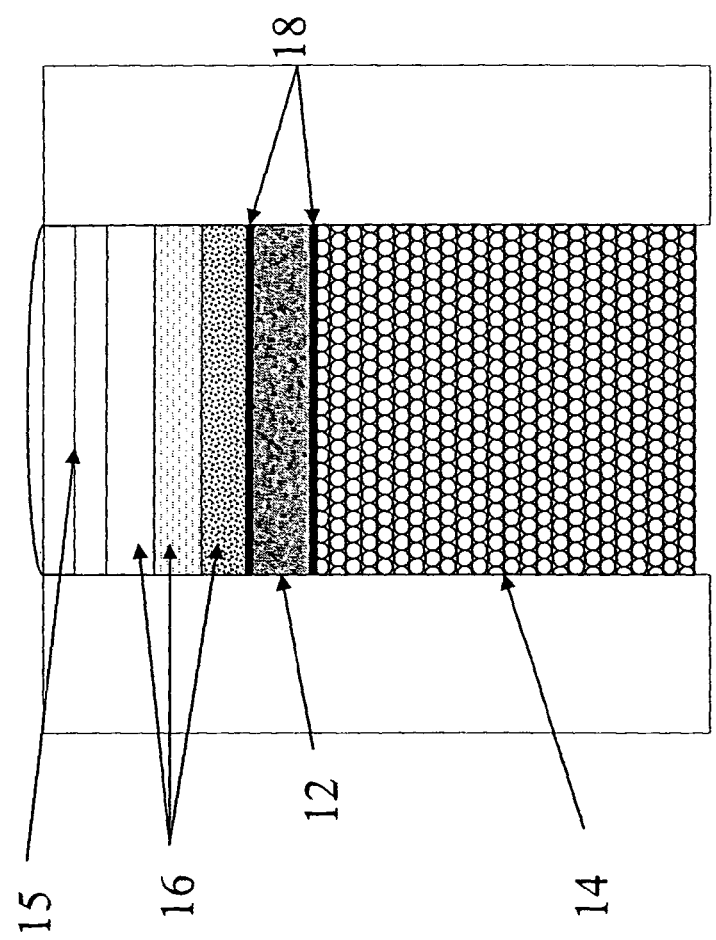
FIG. 3 is a cross-section view of another embodiment of an ultrasound element and associated backing block.

FIG. 3 shows another embodiment of an element of a transducer. The element includes a plurality of matching layers 16. A window or lens 15 is shown positioned over the matching layers 16. The backing block 14 is shown as a composite of silicone microspheres in an epoxy (or other nonsilicone) matrix.

Figure 2:
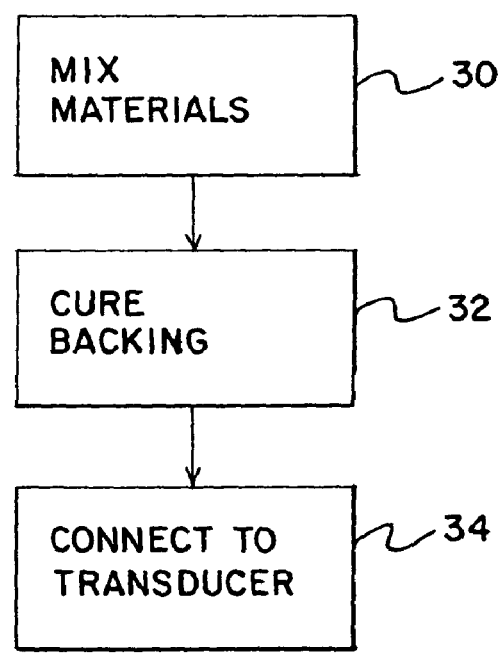
FIG. 2 is a flow chart diagram of one embodiment of a method for manufacturing a backing block for a transducer.

FIG. 2 shows a method of manufacturing an ultrasound transducer backing material for ultrasound transmission and/or reception. Additional, different or fewer acts may be provided, such as not performing one or more of the casting, molding and centrifuging acts described below. The method shown in FIG. 2 is used to form the backing block composite material described above with reference to FIG. 1, or a different backing block composite material.

In act 30, two or more different materials are mixed to form a composite. For example, roughly equal volumes of about 13 micron silicone rubber microspheres and a low-viscosity, curable two-part epoxy resin are homogenized by shear mixing, such as with a mechanical or motor-driven mixer. In one embodiment, one of the materials, such as the silicone, is in a solid phase or has been previously cured. As a result, the composite material contains a plurality of particles used for forming the pockets 20. The other material is in liquid form to allow mixing and curing. Different polymers or other types of different materials in either of liquid or solid phase may be mixed. For example, particles of a non-polymeric material having less than 20 microns along a maximum dimension may be mixed into a liquid polymer or other curable resin.

The mixture is degassed, such as by using vacuum degassing. Any air or other gas expands in response to a decreased pressure around the mixture. The expanded bubbles migrate to the surface, releasing the gas from the mixture. The degassed mixture is then cast or injected into a mold. In one example, the mold or casting plate includes a rectangular volume associated with the simple shape of the backing block 14. In alternative embodiments, the mold includes various shaping elements or other structures desired to be formed within the backing block 14. In yet other embodiments, stiffeners or other inserts to be positioned within the backing block 14 are positioned within the mold. For example, a metallic insert for heat dissipation is aligned within the mold, the uncured composite is added, and the backing block is then cured around the in situ stiffener. In yet other alternative embodiments, any stiffeners, inserts or other structures are added after curing. Shaping for the additional structures or for other reasons is formed by machining after curing in these alternative embodiments.

In one embodiment, the cast mixture is centrifuged to maximize the volume fraction of the filler particles. Centrifuging a low-density filler like silicone creates an outward or bottom layer of primarily epoxy and a top layer with air, or gas voids. The desired backer material is then recovered from the intermediate layer, which is neither epoxy-rich, nor laced with gas voids. Higher-density materials tend to migrate to the bottom or outer layer, and lower-density materials tend to migrate towards a top or innermost layer of the centrifuged casting. Where any inserts or shaping is provided in the mold, the inserts and shaping are arranged to account for any removal of epoxy-rich or voidy material after centrifuging, either before or after curing.

In act 32, the backing material or mixture is cured. For example, the mixture is cured after casting and centrifuging. In alternative embodiments, the mixture is cured without centrifuging. In another embodiment, the mixture cures during centrifuging. In yet another embodiment, the mold or casting plate is placed within an oven for curing at a temperature above room temperature. In alternative embodiments, the curing occurs at room temperature or less than room temperature. The cure is in response to the chemical reaction of the two-part epoxy, evaporation of solvent, reaction with air, or combinations thereof.

The cured mixture is then finished to a desired shape of the backing block 14. For example, the upper and lower surfaces associated with the centrifuging are shaved off to remove the undesired portions of the mixture. Etching, dicing, cutting, grinding, and/or other processes are used in alternative embodiments to shape the cured mixture into the desired backing block 14.

In act 34, the cured mixture is connected as a backing block to a transducer. For example, the backing block 14 is used as a plate for stacking the other elements of the transducer, such as for stacking the plate of PZT ceramic and associated electrodes 18 as well as one or more matching layers. The transducer stack is then bonded. In one embodiment, the backing block 14 of the composite material is bonded to a polyester, polyamide, or other metallized flex circuit film comprising the electrode 18. Since the matrix 22 is typically composed of a bondable resin, epoxy or other bonding as normally used or later developed readily connects the backing block 14 to the transducer element 12. In alternative embodiments, other types of connection, such as mechanical connections, are provided.

Figure 4:
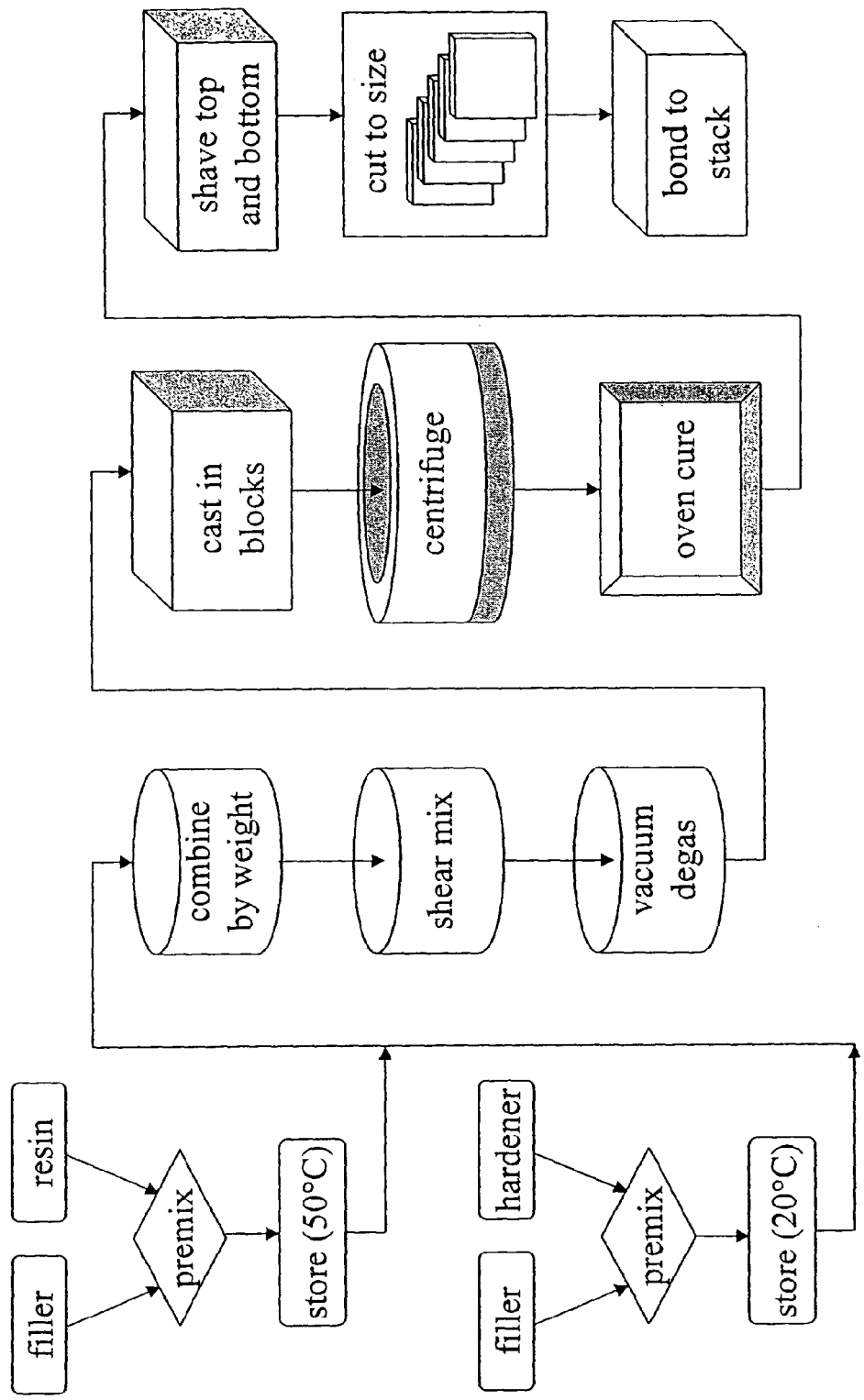
FIG. 4 is a flow chart diagram of another embodiment of a method for manufacturing a backing block for a transducer.

FIG. 4 shows another flow chart of a method for manufacturing a transducer with a composite backing block. The silicone microspheres are added as filler to both the resin and hardener in stored premixes.

While the invention has been described above by reference to various embodiments, it should be understood that many changes and modifications can be made without departing from the scope of the invention. For example, different materials for the filler or matrix may be provided, such as different polymers or non-polymeric materials. Three or more different materials are used for the composite in other examples. As another example, densities and associated impedances greater than ten percent in difference may be provided. As yet another example, larger or smaller filler particles than the 20 or 13 microns discussed herein may be used.

It is therefore intended that the foregoing detailed description be regarded as illustrative rather than limiting, and that it be understood that it is theses following claims, including all equivalents, that are intended to define the spirit and scope of this invention.

We claim:

1. An ultrasound transducer for ultrasound transmission and/or reception, the ultrasound transducer comprising:
   an array of transducer elements; and
   a backing block adjacent the elements, the backing block comprising a composite of first and second materials, the first material including a plurality of pockets filled with but not bonded to particles comprised of the second material;
   wherein the pockets are less than 20 µm along a maximum dimension.

2. The transducer of claim 1 wherein the first material comprises epoxy and the second material comprises silicone microspheres.

3. The transducer of claim 1 wherein the pockets are less than 13 μm along a maximum dimension.

4. The transducer of claim 1 wherein a density of the first material is within 10 percent of a same density as the second material.

5. The transducer of claim 1 wherein the first material comprises a first fraction of the volume of the backing block and the second material comprises a second volume fraction of the backing block, the first volume fraction being within 10 percent of a second volume fraction.

6. The transducer of claim 1 wherein the first material has a first acoustic impedance to ultrasound and the second material has a second acoustic impedance to ultrasound, the first acoustic impedance being within 10 percent of the second acoustic impedance.

7. The transducer of claim 1 wherein each of the plurality of pockets comprises a substantially spherical volume.

8. The transducer of claim 1 wherein the first material is incompatible with the second material.

9. The transducer of claim 1 wherein the pockets of the second material are enclosed within the first material, the second material unbound to the first material.

10. The transducer of claim 9 wherein the pockets of the second material are operable to generate friction against the first material in response to applied acoustic energy.

11. The transducer of claim 1 wherein the first material interconnects throughout the backing block, the backing block having a stiffness about the same as the first material.

12. An ultrasound transducer for ultrasound transmission or reception, the ultrasound transducer comprising:
   an array of transducer elements; and
   a backing block adjacent the elements, the backing block comprising a composite of first and second materials, the second material incompatible with the first material wherein the second material is operable to generate friction with the first material in response to applied acoustic energy, wherein the first and second materials comprise different polymers.

13. The transducer of claim 12 wherein the backing block includes pockets of the second material within the first material.

14. The transducer of claim 12 wherein the first material has a substantially different hardness but substantially the same acoustic impedance as the second material.

15. An ultrasound transducer for ultrasound transmission or reception, the ultrasound transducer comprising:
   an array of transducer elements; and
   a backing block adjacent the elements, the backing block comprising a composite of solid silicone and a cured, nonsilicone resin, the solid silicone unbonded with and in pockets of the resin.

16. The transducer of claim 15 wherein volumes of the silicone are enclosed within the resin.

17. The transducer of claim 15 wherein the backing block is substantially free of plasticizer.

18. The transducer of claim 15 wherein the composite has an acoustic impedance of about 1-2 MRayl.

* * * * *